United States Patent [19]

Shiber

[11] Patent Number: 4,957,482
[45] Date of Patent: * Sep. 18, 1990

[54] ATHERECTOMY DEVICE WITH A POSITIVE PUMP MEANS

[75] Inventor: Samuel Shiber, Woburn, Mass.

[73] Assignee: Surgical Systems & Instruments, Inc., Mundelein, Ill.

[*] Notice: The portion of the term of this patent subsequent to Jun. 27, 2006 has been disclaimed.

[21] Appl. No.: 326,967

[22] Filed: Mar. 22, 1989

Related U.S. Application Data

[63] Continuation-in-part of Ser. No. 286,509, Dec. 19, 1988, Pat. No. 4,894,051, which is a continuation-in-part of Ser. No. 243,900, Sep. 13, 1988, Pat. No. 4,886,490, which is a continuation-in-part of Ser. No. 78,042, Jul. 27, 1987, Pat. No. 4,819,634, and a continuation-in-part of Ser. No. 205,479, Jun. 13, 1988, Pat. No. 4,883,458, and a continuation-in-part of Ser. No. 225,880, Jul. 29, 1988, Pat. No. 4,842,579, which is a continuation-in-part of Ser. No. 18,083, Feb. 24, 1987, which is a continuation-in-part of Ser. No. 874,546, Jun. 16, 1986, Pat. No. 4,732,154, which is a continuation-in-part of Ser. No. 609,846, May 14, 1984, abandoned.

[51] Int. Cl.$^5$ ............................................. A61B 17/00
[52] U.S. Cl. ...................................... 604/22; 606/159
[58] Field of Search ................. 606/159, 170, 180; 604/22, 264, 266, 268; 128/751–755

[56] References Cited

U.S. PATENT DOCUMENTS

| | | | |
|---|---|---|---|
| 2,505,358 | 4/1950 | Gusberg et al. | 128/751 |
| 3,614,953 | 10/1971 | Moss | 606/159 |
| 3,902,498 | 9/1975 | Niederer | 606/170 |
| 4,020,847 | 5/1977 | Clark, III | 606/176 X |
| 4,627,436 | 12/1986 | Leckrone | 606/7 |
| 4,672,962 | 6/1987 | Hershenson | 606/28 |
| 4,700,705 | 10/1987 | Kensey et al. | 606/159 |
| 4,754,755 | 7/1988 | Husted | 606/159 |
| 4,844,064 | 7/1989 | Thimsen et al. | 606/80 |

Primary Examiner—Robert A. Hafer
Assistant Examiner—Lynda M. Cofsky

[57] ABSTRACT

An atherectomy system for cutting, ingesting and removing an obstruction from within a patient's artery, comprising a flexible guide-wire insertable into the artery, a flexible rotary-catheter rotatably disposed and slidable over the flexible guide-wire, a blade forming a distal end of the flexible rotary-catheter having teeth on its periphery which are bent inward, a continuous passage for ingesting the cut obstruction material between the flexible rotary-catheter and the flexible guide-wire, means at the proximal end of the flexible rotary-catheter for rotating it and positive displacement pump means connected to the continuous passage to pull the cut obstruction material proximally.

8 Claims, 1 Drawing Sheet

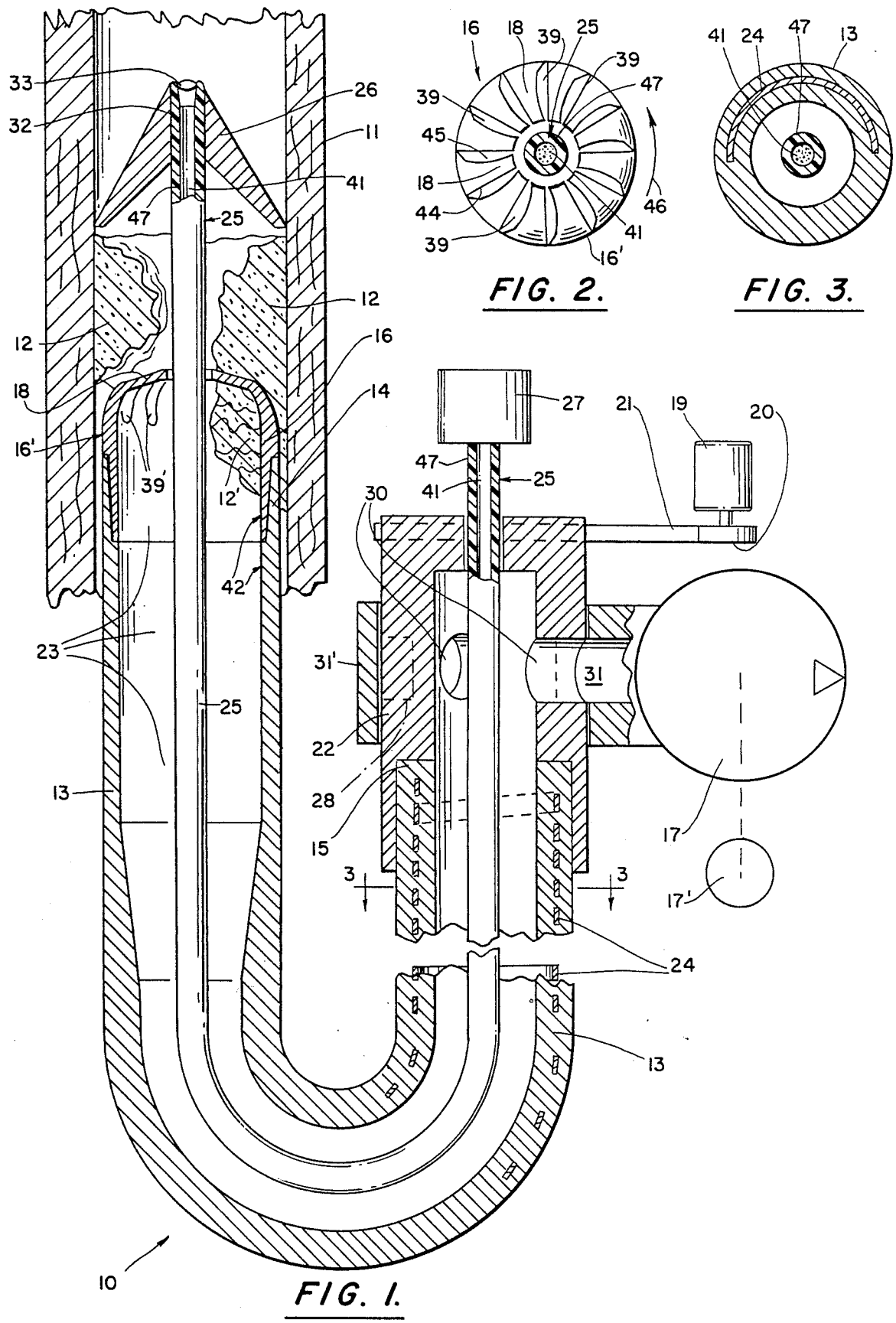

ATHERECTOMY DEVICE WITH A POSITIVE PUMP MEANS

CROSS REFERENCE TO OTHER APPLICATIONS

This application is a continuation in part (CIP) of application Ser. No. 07/286,509 filed 12/19/88 (now U.S. Pat. No. 4,894,051) which is a CIP of application Ser. No. 07/243,900 filed 9/13/88 (now U.S. Pat. No. 4,886,490) which is a CIP of three applications, application Ser. No. 07/078,042 filed 7/27/87 (now U.S. Pat. No. 4,819,634), application Ser. No. 07/205,479 filed 6/13/1988 (now U.S. Pat. No. 4,88,458) and application Ser. No. 07/225,880 filed 7/29/88 (now U.S. Pat. No. 4,842,579). These three applications are CIPs of application Ser. No. 07/018,083 filed 2/24/1987, which is a CIP of application Ser. No. 06/874,546 filed 6/16/1986 (now U.S. Pat. No. 4,732,154) which is a CIP of application Ser. No. 06/609,846 filed 5/14/1984 (abandoned).

All the above applications are being incorporated herein by reference.

BACKGROUND AND OBJECTIVES OF THE INVENTION

With age a large percentage of the population develops arterial obstructions formed by fats, fibrous material and calcified deposits, resulting in a diminished blood circulation. The disturbance to blood flow which these obstructions cause may induce blood clots which further diminish or block the blood flow. When this process occurs in the coronary arteries it is referred to as a heart attack. Presently such obstructions are circumvented by surgically grafting a bypass or they are treated by a catheter equipped with a balloon which is inserted through the arterial system, over a flexible guide-wire, into the obstruction and then inflated to expand the obstruction's lumen (angioplasty). Problems with this treatment are that it injures the arterial wall creating a rough lumen and in certain cases it is ineffective. Further, angioplasty does not remove the obstruction material out of the arterial system, therefore in a case of a heart attack, immediate angioplasty carries the risk of dislodging the blood clot and allowing it to move down stream creating additional blockages.

An objective of the invention is to provide an atherectomy catheter rotatable over a flexible guide-wire, equipped with a rotary cutting means at its distal end, that would cut and ingest the obstruction material, including blood clots if present, create a smooth lumen and not crack the arterial wall.

A further objective of the present invention is to provide suction means to assist the flexible rotary-catheter in ingesting the obstruction material. Preferably, a self regulating suction means that automatically increases and decreases the suction in response to the presence or the absence, respectively, of obstruction material in the flexible rotary-catheter. Thereby, such suction means reduces the amount of blood removed from the patient.

Another objective of the invention is to provide a system that would lend itself to be produceable in diameters down to around 1 mm (millimeter) and a length of up to around a meter, to be able to reach and enter small and remote arteries.

Preferably, the operation of the atherectomy system would resemble the operation of present catheter systems, so that existing skills of the medical staff can be utilized. These and other objectives of the invention will become apparent from the following discussion and the accompanying drawings.

BRIEF DESCRIPTION OF THE FIGURES

FIG. 1 generally shows a cross sectional view of an atherectomy system according to the present invention.

FIG. 2 shows a distal end of the atherectomy system.

FIG. 3 shows a cross sectional view of the atherectomy system along a line 3—3 marked on FIG. 1.

DETAILED DESCRIPTION OF THE DRAWINGS

FIG. 1 shows the atherectomy system 10 for cutting, ingesting and removing an obstruction 12 from within a patient's vessel, an artery 11. As shown in FIG. 1, the atherectomy system comprises several elongated parts in a nested relationship, and their ends shall be referred to as "distal", meaning the end which goes into the artery and "proximal", meaning the other end. Therefor, "distal direction" or the term "distally" shall indicate a general direction from the proximal end to the distal end, and "proximal direction" or "proximally" shall refer to an opposite direction.

The atherectomy system comprises:

A flexible guide-wire 25 which is insertable into the artery. Optionally, the flexible guide-wire is equipped with a distal barrier means in the form of a flexible collapsible umbrella 26 to counter distal movement of surrounding obstruction material while the blade cuts the obstruction material. The flexible guide-wire may also contain an optical fiber bundle 41 in a plastic jacket 47 and a lens 33 at its distal tip. An imaging unit and/or lasar gun 27 may be optically coupled to the proximal end of the optical fiber bundle for analyzing the inside of the artery and/or opening, respectively, a pilot passage for the distal tip of the flexible guide-wire to pass through in a case of complete arterial blockage.

A flexible rotary-catheter 13 is rotatably disposed and slidable over the flexible guide-wire.

A stainless steel hollow blade 16 forms a distal end of the flexible rotary-catheter. The blade has teeth 18 on its periphery which are bent inwardly, toward the center of the blade, to ease insertion through the arteries and to reduce the chance of cutting the wall of the artery during the insertion and cutting operation. A front edge 44 of the teeth is sharpened to cut the obstruction material to pieces 12' which pass into a continuous passage 23 through spaces 39 between the teeth while the blade rotates forward in a direction of arrow 46 (note FIG. 2). A back side of the teeth 45 is dull to allow a backwards rotation while manipulating and advancing the flexible rotary-catheter through the arterial system towards the obstruction with a reduced risk of injuring the arterial wall. The blade has an outer wall 16' which slidingly and rotatably bears against the artery spreading the contact force on a relatively large area and thereby minimizing the damage to the artery. A rotating inner-wall 42 is formed by the inside surface of the flexible rotary-catheter.

The continuous passage 23 is defined between the rotating inner-wall and the flexible guide-wire, and the relative motion between the flexible rotary-catheter and the flexible guide-wire mechanically acts on the ingested obstruction material in the continuous passage and enables it to move towards the proximal end 15 of the flexible rotary-catheter and make room for . additional cut material.

Coupling means affixed to the proximal end of the flexible rotary-catheter in the form of a hub 22 is frictionally engaged with a flat belt 21 which couples the flexible rotary-catheter to a rotating means in the form of a motor 19 having a pulley 20. The proximal end of the flexible guide-wire slidingly and rotatably extends through the hub.

Suction can be applied to the proximal end of the flexible rotary-catheter by, preferably, a positive displacement type suction pump 17, driven by a motor 17'. The suction is applied through ports 30 which alternately communicate with a port 31 formed in a sleeve 31', as the hub rotates in the sleeve 31'. Alternatively, a groove 28 (shown in phantom lines) can provide continuous communication between the continuous passage 23 and the port 31. The suction cooperates with the mechanical action taking place in the continuous passage to move the cut obstruction material 12' proximally. A positive displacement pump such as a piston pump or a peristalic pump tends to self regulate the evacuation process. The amount of blood removed is limited by the volume that is positively displaced by the pump. When only blood is present, and since blood flows relatively easily, the negative pressure in the continuous passage will drop. As obstruction material enters the continuous passage the negative pressure rises and pulls the cut material proximally. The level of negative pressure can be limited by a relief valve in the pump. The action of the pump can be synchronized with the actual cutting action of the blade 16, or otherwise selectively controlled to avoid excessive blood removal.

Torque generated by the motor is partially dissipated by frictional losses along the flexible rotary-catheter, therefore, the flexible rotary-catheter can be manufactured with an increased wall thickness and increased torque carrying capacity at the vicinity of its proximal end compared with the same at its distal end (note FIG. 1), and the wall can be reinforced by a spiral means in the form of metal ribbon 24 (note FIGS. 1 and 3). The atherectomy system can be manufactured in different diameters and lengths depending on the size and site of artery that it is intended for and on whether the system is to be used percutaneously (that is through the skin) or intra-operatively (that is when the artery is surgically exposed for inserting the system).

A process for removing an obstruction from a artery with an atherectomy system, comprises the following steps:

Conventionally inserting into an artery, into an obstruction, a flexible guide-wire.

Advancing over the flexible guide-wire a blade located at a distal end of an atherectomy catheter.

Advancing the blade to the obstruction and cutting the obstruction. During the operation the flexible guide-wire and the flexible introducer sleeve (if present) are prevented from being rotationally dragged by the blade. Fluid can be delivered to the obstruction site through the flexible sleeve, around the atherectomy catheter. Such fluid can lubricate and cool the cutting process and provide a medium for flushing particles of obstruction material into the atherectomy catheter, especially in conjunction with suction, preferably applied to the proximal end of the atherectomy catheter by a positive displacement pump means. The fluid may be radio-opaque to assist x-raying the process. Prior to cutting, fluid can also be delivered through the atherectomy catheter.

Removing the catheter containing the cut obstruction material out of the artery.

The sequence of insertion of the components into the artery may vary depending on the nature and the location of the obstruction and the preferences of the medical staff. Additional steps may be added to assist the process. For example, a standard guiding catheter, which is either straight or pre-bent, may be inserted into the artery to assist in bringing the flexible-guide-wire and the atherectomy catheter to the obstruction site.

When an arterial obstruction is further blocked by a fresh blood clot, as is often the case in a heart attack, the flexible guide-wire can usually be inserted through the fresh clot and the atherectomy system, preferably while employing suction, can be used to clear the clot in order to restore blood flow through the artery and alleviate the acute heart attack. Then the system can be utilized to cut the underlying atherosclorotic obstruction providing a long term correction to the condition that induced the attack.

While the present invention has been illustrated by a single embodiment, it should be understood that various modifications and substitutions may be made without departing from the spirit of the invention or the scope of the claims.

I claim:

1. An atherectomy system for cutting, ingesting and removing an obstruction from within a patient's artery, comprising in combination:
    a flexible guide-wire insertable into said artery,
    a flexible rotary-catheter being rotatably disposed and slidable over said flexible guide-wire,
    a blade forming a distal end of said flexible rotary-catheter having at least one tooth on its periphery which is bent inward,
    a continuous passage surrounding said flexible guide-wire for ingesting the cut obstruction material, said continuous passage being defined between said flexible rotary-catheter and said flexible guide-wire,
    coupling means at said proximal end of said flexible rotary-catheter for coupling it to a rotating means, and
    suction means connected to said continuous passage to pull said cut obstruction material proximally.

2. An atherectomy system as in claim 1, wherein said suction is provided by a positive displacement pump means.

3. An atherectomy system as in claim 1, wherein said flexible rotary-catheter has an increased wall thickness and increased torque carrying capacity at the vicinity of its proximal end compared with the same at its distal end.

4. An atherectomy system as in claim 1, wherein said flexible rotary-catheter has a wall reinforced with a spiral member.

5. An atherectomy system as in claim 4, wherein said spiral member is made of metal.

6. An atherectomy system as in claim 4, wherein said spiral member is made of a flat metal ribbon.

7. An atherectomy system as in claim 1, said flexible guide-wire having distal barrier means to counter distal movement of surrounding obstruction material while said blade cuts the obstruction material.

8. An atherectomy system as in claim 1, said flexible guide-wire containing a optical fiber.

* * * * *